(12) United States Patent
Bloom (10) Patent No.: US 10,479,989 B2
(45) Date of Patent: Nov. 19, 2019

(54) COMPOSITIONS FOR MAKING RANDOM CODON-MUTANT LIBRARIES AND USES THEREOF

(71) Applicant: FRED HUTCHINSON CANCER RESEARCH CENTER, Seattle, WA (US)

(72) Inventor: Jesse D. Bloom, Seattle, WA (US)

(73) Assignee: Fred Hutchinson Cancer Research Center, Seattle, WA (US)

( * ) Notice: Subject to any disclaimer, the term of this patent is extended or adjusted under 35 U.S.C. 154(b) by 319 days.

(21) Appl. No.: 14/898,444

(22) PCT Filed: Jun. 13, 2014

(86) PCT No.: PCT/US2014/042406
§ 371 (c)(1),
(2) Date: Dec. 14, 2015

(87) PCT Pub. No.: WO2014/201416
PCT Pub. Date: Dec. 18, 2014

(65) Prior Publication Data
US 2016/0145603 A1    May 26, 2016

Related U.S. Application Data

(60) Provisional application No. 61/835,377, filed on Jun. 14, 2013.

(51) Int. Cl.
*C12N 15/10* (2006.01)
*C12N 15/67* (2006.01)

(52) U.S. Cl.
CPC ....... *C12N 15/1031* (2013.01); *C12N 15/102* (2013.01); *C12N 15/67* (2013.01)

(58) Field of Classification Search
None
See application file for complete search history.

(56) References Cited

U.S. PATENT DOCUMENTS

| | | | |
|---|---|---|---|
| 6,242,222 B1 * | 6/2001 | Gifford | C12N 15/102 435/6.1 |
| 7,879,582 B2 | 2/2011 | Milano et al. | |
| 8,383,346 B2 | 2/2013 | Colbeck et al. | |
| 2004/0091886 A1 | 5/2004 | Moore et al. | |
| 2010/0093560 A1 * | 4/2010 | Colbeck | C12N 15/102 506/9 |

FOREIGN PATENT DOCUMENTS

EP    2390322 A1    11/2011

OTHER PUBLICATIONS

Edelheit et al. (BMC biotechnology 9.1 (2009): 61) (Year: 2009).*
Bloom et al., "An Experimentally Determined Evolutionary Model Dramatically Improves Phylogenetic Fit," *Mol. Biol. Evol.* 31(8):1956-1978 (May 24, 2014).

* cited by examiner

*Primary Examiner* — Tracy Vivlemore
*Assistant Examiner* — Sahana S Kaup
(74) *Attorney, Agent, or Firm* — Seed IP Law Group LLP

(57) ABSTRACT

The present disclosure relates to compositions and methods for randomly introducing codon-mutations in a target nucleic acid molecule and, more particularly, using wild-type and triplet-randomized oligonucleotides to introduce mutations uniformly across a target nucleotide of interest in a controlled fashion and with a low rate of insertions or deletions.

18 Claims, 7 Drawing Sheets
Specification includes a Sequence Listing.

SEQUENCE LISTING

<160> NUMBER OF SEQ ID NOS: 2

<210> SEQ ID NO 1
<211> LENGTH: 46
<212> TYPE: DNA
<213> ORGANISM: Artificial Sequence
<220> FEATURE:
<223> OTHER INFORMATION: Primer

<400> SEQUENCE: 1
catgatcgtc tcagggagca aaagcagggt agataatcac tcacag     46

<210> SEQ ID NO 2
<211> LENGTH: 43
<212> TYPE: DNA
<213> ORGANISM: Artificial Sequence
<220> FEATURE:
<223> OTHER INFORMATION: Primer

<400> SEQUENCE: 2
catgatcgtc tcgtattagt agaaacaagg gtattttct tta     43

COMPOSITIONS FOR MAKING RANDOM CODON-MUTANT LIBRARIES AND USES THEREOF

CROSS REFERENCE TO RELATED APPLICATION

This application claims the benefit under 35 U.S.C. § 119(e) to U.S. Provisional Application No. 61/835,377 filed on Jun. 14, 2013, which application is incorporated by reference herein in its entirety.

STATEMENT OF GOVERNMENT INTEREST

This invention was made with government support under GM102198 awarded by the National Institutes of Health. The government has certain rights in the invention.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 360056_418USPC_SEQUENCE_LISTING.txt. The text file is 1 KB, was created on Dec. 9, 2015, and is being submitted electronically via EFS-Web.

BACKGROUND

Technical Field

The present disclosure relates to compositions and methods for randomly introducing codon-mutations in a target nucleic acid molecule and, more particularly, using wild-type and triplet-randomized oligonucleotides to introduce mutations uniformly across a target nucleotide of interest in a controlled fashion and with a low rate of insertions or deletions.

Description of the Related Art

Libraries of mutant genes are generated for use in a wide-variety of biology and bioengineering applications, such as in directed evolution of enzymes and biotherapeutics (Cherry and Fidantsef, *Curr. Opin. Biotechnol.* 14:438, 2003; Jäckel et al., *Annu. Rev. Biophys.* 37:153, 2008), creation of computationally-focused protein libraries (Lutz and Patrick, *Curr. Opin. Biotechnol.* 15:291, 2004), stabilization of proteins (Eijsink et al., *Biomol. Eng.* 22:21, 2005), and examination of structure-function relationships by deep-sequencing (Araya and Fowler, *Trends Biotechnol.* 29:435, 2011). In essence, mutant libraries are useful for the study and engineering of any gene property that can be screened or selected for in a relatively high-throughput fashion.

Mutant libraries are considered most effective for these purposes when most variants are mutated at a modest level. For example, introduction of an average of between one and ten amino-acid mutations per gene (most typically around three) is preferred (Cirino et al., "Generating mutant libraries using error-prone PCR." In *Directed Evolution Library Creation*, pp. 3-9, Humana Press, 2003) because this strikes a balance between introducing sufficient diversity and introducing too many mutations that may result in mostly inactive variants. The probability that a protein retains its proper fold declines exponentially with the number of mutations, so highly mutated variants are often nonfunctional (Drummond et al., *J. Mol. Biol.* 350:806, 2005).

But, the current techniques for creating such mutant libraries are limited. For example, existing techniques for mutating genes across their entire length rely on processes that introduce mutations at the nucleotide level, such as by error-prone PCR or chemical mutagenesis (Cirino et al., 2003). As a result, the only mutant codons that are introduced at an appreciable rate are those that differ from the wild-type codon by just a single-nucleotide. This is because nucleotide-level mutagenesis will only rarely mutate two adjacent nucleotides, and is even less likely to mutate all three nucleotides in a codon (see Miyazaki and Arnold, *J. Mol. Evol.* 49:716, 1999).

Another established technique does allow the introduction of mutations at the codon level, but only at a small number of pre-selected sites (Georgescu et al., "Saturation mutagenesis." In *Directed Evolution Library Creation*, pp. 75-83, Humana Press, 2003). This technique uses PCR with oligonucleotides that have been randomized at triplet sites. If, for example, a triplet is randomized to NNN (wherein N is taken to denote any nucleotide), then all 64 codons will appear in the library at that one site. However, these methods lead to rapid accumulation of insertions and deletions (which generally inactivate a protein) as the number of mutated sites increase, rendering these methods ineffective for more than a few positions. Hence, such techniques can only be used to fully randomize one or a small number of codons.

In view of the limitations associated with the production of mutant libraries, there is a need in the art for alternative methods for creating mutant libraries in which codon mutations are introduced across the full length of a gene or other nucleic acid of interest at a controlled rate so that the typical clone will have a small number of codon mutations. The present disclosure meets such needs, and further provides other related advantages.

DETAILED DESCRIPTION

In one aspect, the present disclosure provides compositions and methods for randomly introducing codon-mutations into a target nucleic acid molecule. In certain embodiments, a plurality of mutagenic oligonucleotides comprising a randomized codon such that each oligonucleotide randomizes one to three codons of a reference nucleic acid molecule template to introduce mutations uniformly across a target nucleic acid molecule of interest in a controlled fashion and with a low rate of insertions or deletions.

Prior to setting forth this disclosure in more detail, it may be helpful to an understanding thereof to provide definitions of certain terms to be used herein. Additional definitions are set forth throughout this disclosure.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the terms "about" and "consisting essentially of" mean±20% of the indicated range, value, or structure, unless otherwise indicated. It should be understood that the terms "a" and "an" as used herein refer to "one or more" of the enumerated components. The use of the alternative (e.g., "or") should be understood to mean either one, both, or any combination thereof of the alternatives or enumerated components. As used herein, the terms "include," "have" and "comprise" are used synonymously, which terms and variants thereof are intended to be construed as non-limiting.

As used herein, "nucleic acid" or "nucleic acid molecule" refers to any of deoxyribonucleic acid (DNA), ribonucleic acid (RNA), oligonucleotides, fragments generated by the polymerase chain reaction (PCR), and fragments generated by any of ligation, scission, endonuclease action, and exonuclease action. In certain embodiments, the nucleic acids of the present disclosure are produced by PCR. Nucleic acids may be composed of monomers that are naturally occurring nucleotides (such as deoxyribonucleotides and ribonucleotides), analogs of naturally occurring nucleotides (e.g., α-enantiomeric forms of naturally-occurring nucleotides), or a combination of both. Modified nucleotides can have modifications in sugar moieties or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety may be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids" (PNAs), which comprise naturally occurring or modified nucleic acid bases attached to a polyamide backbone. Nucleic acid molecules can be either single stranded or double stranded.

Further, an "isolated nucleic acid molecule" refers to a polynucleotide molecule in the form of a separate fragment or as a component of a larger nucleic acid construct, which has been separated from its source cell (including the chromosome it normally resides in) at least once in a substantially pure form. For example, a DNA molecule that encodes a recombinant polypeptide, peptide, or variant thereof, which has been separated from a cell or from the genomic DNA of a cell, is an isolated nucleic acid molecule. Another example of an isolated nucleic acid molecule is a bacteriophage promoter (e.g., T5 or T7), or nucleic acid expression control sequence, which can be cloned into a vector capable of replication in a suitable host cell. Still another example of an isolated nucleic acid molecule is a chemically synthesized or PCR synthesized nucleic acid molecule.

As used herein, "mutation" refers to a change in the sequence of a nucleic acid molecule or polypeptide molecule as compared to a reference or wild-type nucleic acid molecule or polypeptide molecule, respectively. A mutation can result in several different types of change in sequence, including substitution, insertion or deletion of nucleotide(s) or amino acid(s). In other embodiments, a mutation is a substitution of one or more nucleotides or residues.

As used herein, a "codon mutant library" refers to a collection of nucleic acid molecule sequences or fragments that may be incorporated into a vector, which may be further transformed or transfected into an appropriate host cell. The target nucleic acid molecules of this disclosure may be introduced into a variety of different vector backbones (such as plasmids, cosmids, viral vectors, or the like) so that recombinant production of a library can be maintained in a host cell of choice (such as bacteria, yeast, mammalian cells, plant cells, or the like). The reference nucleic acid molecule templates that are incorporated into a vector may be from natural samples (e.g., a genome), or the nucleic acid molecules may be synthetic samples (e.g., PCR product), recombinant samples, or a combination thereof. Prior to insertion into a vector, a plurality of nucleic acid molecules may undergo additional reactions for optimal cloning, such as mechanical shearing, specific cleavage with restriction endonucleases, or addition of short nucleotide sequences to introduce, for example, a restriction endonuclease site.

The term "construct" refers to any polynucleotide that contains a recombinant nucleic acid. A construct may be present in a vector (e.g., a bacterial vector, a viral vector) or may be integrated in a genome, for example. A "vector" is a nucleic acid molecule that is capable of transporting another nucleic acid. Vectors may be, for example, plasmids, cosmids, viruses, or phage.

The term "operably-linked" refers to the association of nucleic acid sequences on a single nucleic acid fragment so that the function of one is affected by the other. For example, a promoter is operably-linked with a coding sequence when it is capable of affecting the expression of that coding sequence (i.e., the coding sequence is under the transcriptional control of the promoter). "Unlinked" means that the associated genetic elements are not closely associated with one another and the function of one does not affect the other.

As used herein, "expression vector" refers to a DNA construct containing a nucleic acid molecule that is operably-linked to a suitable control sequence capable of effecting the expression of the nucleic acid molecule in a suitable host. Such control sequences include a promoter to effect transcription, an optional operator sequence to control such transcription, a sequence encoding suitable mRNA ribosome binding sites, and sequences which control termination of transcription and translation. The vector may be a plasmid, a phage particle, or simply a potential genomic insert. Once transformed into a suitable host, the vector may replicate and function independently of the host genome, or may, in some instances, integrate into the genome itself. In the present specification, "plasmid," "expression plasmid," and "vector" are often used interchangeably as the plasmid is the most commonly used form of vector at present. However, this disclosure is intended to include such other forms of expression vectors that serve equivalent functions and which are, or become, known in the art.

The term "expression", as used herein, refers to the process by which a polypeptide is produced based on the nucleic acid sequence of a gene. The process includes both transcription and translation.

The term "introduced" in the context of inserting a nucleic acid sequence into a cell, means "transfection", or 'transformation" or "transduction" and includes reference to the incorporation of a nucleic acid sequence into a eukaryotic or prokaryotic cell wherein the nucleic acid sequence may be incorporated into the genome of the cell (e.g., chromosome, plasmid, plastid, or mitochondrial DNA), converted into an autonomous replicon, or transiently expressed (e.g., transfected mRNA).

As used herein, the term "isolated" refers to a substance that has been removed from the source in which it naturally occurs. A substance need not be purified in order to be isolated. For example, a protein produced in a host cell is considered isolated when it is removed or released from the cell. A protein contained within a crude cell lysate fraction is considered "isolated" for purposes of the present disclosure. Further, an "isolated nucleic acid molecule" refers to a polynucleotide molecule in the form of a separate fragment or as a component of a larger nucleic acid construct, which has been separated from its source cell, including the chromosome it normally resides in, at least once. For example, a DNA molecule that encodes a recombinant polypeptide, peptide, or variant thereof, which has been separated from the genomic DNA of a cell, is an isolated DNA molecule.

As used herein, the term "purified" refers to a substance that has been rendered at least partially free of contaminants and other materials that typically accompany it. Substances can be purified to varying degrees. A substance is "substantially pure" when a preparation or composition of the substance contains less than about 1% contaminants. A substance is "essentially pure" when a preparation or composition of the substance contains less than about 5% contaminants. A substance is "pure" when a preparation or composition of the substance contains less than about 2% contaminants. For substances that are "purified to homogeneity," contaminants cannot be detected with conventional analytical methods.

The term "recombinant" refers to a polynucleotide or polypeptide that does not naturally occur in a host cell. A recombinant molecule may contain two or more naturally-occurring sequences that are linked together in a way that does not occur naturally. A recombinant cell contains a recombinant polynucleotide or polypeptide.

As used herein, the terms "percent sequence identity," "percent identity," and "% identity" refer to comparisons between polynucleotide sequences or polypeptide sequences, and are determined by comparing two optimally aligned sequences over a comparison window, wherein the portion of the polynucleotide or polypeptide sequence in the comparison window may comprise additions or deletions (i.e., gaps) as compared to the reference sequence in order to effect optimal alignment. Percent identity is calculated by dividing the number of matched portions in the comparison window by the total number of positions in the comparison window, and multiplying by 100. The number of matched positions in the comparison window is the sum of the number of positions of the comparison polynucleotide or polypeptide in the window that are identical in sequence to the reference polynucleotide or polypeptide and the number of positions of the reference polynucleotide or polypeptide in the comparison window that align with a gap in the comparison polynucleotide or polypeptide. Determination of optimal alignment and percent sequence identity is performed using the BLAST and BLAST 2.0 algorithms (see, e.g., Altschul et al., *J. Mol. Biol.* 215:403, 1990; Altschul et al., *Nucleic Acids Res.* 25:3389, 1997). Software for performing BLAST analyses is publicly available through the National Center for Biotechnology Information website.

Briefly, the BLAST analyses involve first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff and Henikoff, *Proc. Nat'l Acad. Sci. USA* 89:10915, 1989). In a preferred embodiment, BLAST algorithm parameters set a default parameters are used to identify percent identity of a target nucleic acid molecule or a target polypeptide molecule as compared to a reference nucleic acid molecule or a reference polypeptide molecule, respectively.

Optimal alignment of sequences for comparison can be conducted, e.g., by the local homology algorithm of Smith and Waterman, *Adv. Appl. Math.* 2:482, 1981; by the homology alignment algorithm of Needleman and Wunsch, *J. Mol. Biol.* 48:443, 1970; by the search for similarity method of Pearson and Lipman, *Proc. Nat'l Acad. Sci. USA* 85:2444, 1988; by computerized implementations of these algorithms (GAP, BESTFIT, FASTA, and TFASTA in the GCG Wisconsin Software Package); or by visual inspection (see, generally, Current Protocols in Molecular Biology, F. M. Ausubel et al., eds., Current Protocols, a joint venture between Greene Publishing Associates, Inc. and John Wiley & Sons, Inc., 1995 Supplement).

As used herein, the term "reference sequence" refers to a specified sequence to which another sequence is compared. A reference sequence may be a subset of a larger sequence, for example, a segment of a full-length gene or polypeptide sequence. Generally, a reference sequence is at least 20 nucleotide or amino acid residues in length, at least 25 residues in length, at least 50 residues in length, or the full length of the nucleic acid or polypeptide. Since two polynucleotides or polypeptides may each (1) comprise a sequence (i.e., a portion of the complete sequence) that is similar between the two sequences, and (2) may further comprise a sequence that is divergent between the two sequences, sequence comparisons between two (or more) polynucleotides or polypeptide are typically performed by comparing sequences of the two polynucleotides over a comparison window to identify and compare local regions of sequence similarity. The term "reference sequence" is not intended to be limited to wild-type sequences, and can include engineered, variant, or altered sequences.

In certain embodiments, the instant disclosure provides a method for making a plurality of variant nucleic acid molecules, comprising (a) amplifying a reference nucleic acid molecule template with a plurality of forward mutagenic oligonucleotides to produce a first plurality of forward mutagenic fragments and separately amplifying the reference nucleic acid molecule template with a plurality of reverse mutagenic oligonucleotides to produce a first plurality of reverse mutagenic fragments, wherein the reference nucleic acid molecule template comprises a plurality of codons that encode a reference polypeptide and wherein each of the plurality of forward and reverse mutagenic oligonucleotides comprise a randomized codon such that each oligonucleotide randomizes one to three codons and the oligonucleotides comprise from nine to 100 nucleotides; (b) purifying the first plurality of forward and reverse mutagenic fragments and mixing the purified first plurality of forward and reverse mutagenic fragments to produce a first mixed mutagenic nucleic acid molecule fragment template composition; and (c) joining the mixed nucleic acid molecule fragments of the first mixed mutagenic nucleic acid molecule fragment template composition by amplifying with the plurality of forward and reverse mutagenic oligonucleotides from step (a) to produce a first plurality of joined mutagenic nucleic acid molecules; thereby introducing a controlled number of codon variants across the length of the reference nucleic acid molecule template. In certain embodiments, two or three adjacent or separated codons are randomized within each oligonucleotide simultaneously mutate two or three codons.

In further embodiments, the method further comprises purifying the first plurality of joined mutagenic nucleic acid molecules and repeating steps (a) through steps (c) of claim 1 to produce a second plurality of joined mutagenic nucleic acid molecules; or the method further comprises purifying the second plurality of joined mutagenic nucleic acid molecules and repeating steps (a) through steps (c) of claim 1 to produce a third plurality of joined mutagenic nucleic acid molecules. In further embodiments, steps (a) through steps (c) of claim 1 are repeated 3, 4, 5, 6, 7, 8, 9, 10, 11, 12, 13, 14, 15, 20, 25, 30, 40, 50 or more times by purifying the plurality of joined mutagenic nucleic acid molecules generated in the previous round of the method and performing steps (a) through steps (c). For example, performing the codon mutagenesis method of the instant disclosure three times will result in a library of variant template molecules having about three codon mutants per sequence that are evenly distributed along the full length of the template sequence. In certain embodiments, the number of codon variants introduced comprises from about one to about ten different mutants. In addition, by adding additional rounds of fragment PCR and joining PCR, it is possible to increase the mutation rate. Adjustments in the number of PCR cycles can also alter the mutation rate. Conversely, reduced rounds will lower the mutation rate.

In certain embodiments, any of the aforementioned methods further comprise the step of amplifying the reference nucleic acid molecule template before step (a) with an oligonucleotide complimentary to the 5'-end the reference nucleic acid molecule template and with an oligonucleotide complimentary to the 5'-end the reference nucleic acid molecule template, wherein the 5'-end and 3'-end oligonucleotides comprise a sequence recognized by a restriction endonuclease to produce an end-modified reference nucleic acid molecule template; and purifying the end-modified reference nucleic acid molecule template for use in any of the preceding claims.

Codon sites may also be mutated to other triplets depending on the desired amino-acid mutations (e.g., NNK introduces all 20 amino acids but fewer stop codons, NTN introduces mostly aliphatic amino-acids, and other degenerate triplets introduce other specific subsets of amino acids (Mason et al., "Considerations in the design and optimization of coiled coil structures." In *Protein Engineering Protocols*, pages 35-70, Springer, 2007)). In another example, a codon may be mutated to YTN (where Y stands for C or T) so that codon will be mutated to phenylalanine and leucine. Any rational approach to identify a possible set of ideal amino acids at each position may be used to design mutagenic oligonucleotides of interest to introduce different codon mutants throughout the length of a template molecule, while still controlling the overall mutation rate as described herein.

As used herein, the symbol W means nucleotides A or T; S means nucleotides C or G; M means nucleotides A or C; K means nucleotides G or T; R means nucleotides A or G; Y means nucleotides C or T; B means nucleotides C, G, or T; D means nucleotides A, G, or T; H means nucleotides A, C, or T; V means nucleotides A, C, or G; and N means nucleotides A, C, G, or T.

In certain embodiments, the randomized codon of the forward and reverse mutagenic oligonucleotides is NNN, YTN, NTN, NNW, NNS, NNM, NNK, NNR, NNB, NND, NNV, NNH, BBB, DDD, VVV, HHH, NNA, NNT, NNC, NNG, NAN, NTN, NCN, NGN, ANN, TNN, CNN, GNN or any combination thereof. Furthermore, the approach of the instant disclosure can be used to mutate all codons of a gene as compared to all other codons with equal probability. In certain embodiments, only specific subsets of mutations at a given site can be introduce by using mutagenic oligonucleotides that contain codons with different randomization mutations. In further embodiments, the balance of the different oligonucleotides may be changed (so they are not all equimolar) to mutate some codon sites at a higher rate than others.

In certain embodiments, the randomized codon of the forward and reverse mutagenic oligonucleotides is located in the middle of the oligonucleotide, near the 5'-end of the oligonucleotide, near the 3'-end of the oligonucleotide, or any combination thereof.

In certain embodiments, the mutagenic oligonucleotides comprise from 9 to 50 nucleotides, from 20 to 50 nucleotides, from 30 to 40 nucleotides, or from 15 to 35 nucleotides. In further embodiments, the number of mutations per reference nucleic acid molecule template follows an approximate Poisson distribution, the mutations occur uniformly along the length of the reference nucleic acid molecule template, the mutant codons introduced into the reference nucleic acid molecule template comprise a uniform base composition, the reference nucleic acid molecule templates comprises multiple mutations that are not clustered, or any combination thereof.

EXAMPLES

Example 1

Construction of Influenza NP Codon-Mutant Libraries

A mutant library with an average of three random codon mutations per gene was constructed according to the instant disclosure. Briefly, pools of mutagenic synthetic oligonucleotides as described below were used in iterative rounds of low-cycle PCR to generate mutated fragments that were joined and remutated to create a codon-mutant library with the desired properties.

A 498-residue influenza nucleoprotein (NP) gene was targeted for mutagenesis. Oligonucleotides were designed to contain a randomized NNN nucleotide triplet preceded by the 16 nucleotides upstream of that codon in the NP gene (or its noncoding termini), and followed by the 16 nucleotides downstream of that codon in the NP gene (or its noncoding termini) for each NP gene codon, except for the methionine initiation codon. This yielded a set of 497 oligonucleotides, each of which randomizes a single codon. The oligonucleotides were prepared in a 96-well plate format (Integrated DNA Technologies, Coralville, Iowa), and then combined in equimolar quantities to create a mixture referred to as the forward-mutagenesis (FM) primer pool. Similarly, a reverse-complement of each of these 497 oligonucleotides was designed and prepared, and then combined in equimolar quantities to create a mixture referred to as the reverse-mutagenesis (RM) primer pool. This included a total of 994 oligonucleotides, which were used to prepare two identical libraries in full biological duplicate (aside from using the same oligonucleotide primer pools for each), which began with independent preparations of the plasmid template. To increase the precision of mutagenesis, great care was taken to run PCR reactions with exact reagent volumes. To avoid contamination, all gel-purification steps used an independent gel for each sample, with the relevant equipment thoroughly washed to remove residual DNA from earlier experiments.

End primers were also designed to anneal to the termini of the DNA sequence for the NP viral-RNA, which also contained 6-nucleotide tails preceding overhangs appropriate for BsmBI cloning into the influenza reverse-genetics plasmid pHW2000 (Neumann et al., *Proc. Nat'l. Acad. Sci. USA* 96:9345, 1999; Hoffmann et al., *Proc. Nat'l. Acad. Sci. USA* 97:6108, 2000). These primers are referred to as 5'-BsmBI-Aichi68-NP (catgatcgtctcagggagcaaaagcagggtagataatcactcacag; SEQ ID NO.:1) and as 3'-BsmBI-Aichi68-NP (catgatcgtctcgtattagtagaaacaagggtatttttctta; SEQ ID NO.:2).

PCR reactions were set up to contain 1 μl of 10 ng/μl template pHWAichi68-NP plasmid (Gong et al., eLife, 2013), 25 μl of 2×KOD Hot Start Master Mix (EMD Millipore, Darmstadt, Germany), 1.5 μl each of 10 μM solutions of the end primers 5'-BsmBI-Aichi68-NP and 3'-BsmBI-Aichi68-NP, and 21 μl of water. The following amplicon PCR program was used: (1) 95° C. for 2 minutes; (2) 95° C. for 20 seconds; (3) 70° C. for 1 second; (4) 50° C. for 30 seconds cooling to 50° C. at 0.5° C. per second; (5) 70° C. for 40 seconds; (6) repeat steps (2) through (5) for 24 additional cycles; and (7) hold at 4° C. The linear PCR products were purified over agarose gels using ZymoClean columns (Zymo Research, Irvine, Calif.) and used as templates for the initial round of fragment PCR codon-mutagenesis.

Two fragment PCR reactions were run for each template. The forward-fragment reactions contained 15 μl of 2×KOD Hot Start Master Mix, 2 μl FM primer pool at a total oligonucleotide concentration of 4.5 μM, 2 μl of 4.5 μM 3'-BsmBI-Aichi68-NP, 4 μl of 3 ng/μl of the aforementioned gel-purified linear PCR product template, and 7 μl of water. The reverse-fragment reactions were identical to the forward fragment reactions except that the RM primer pool was substituted for the FM primer pool, and that 5'-BsmBI-Aichi68-NP was substituted for 3'-BsmBI-Aichi68-NP. The PCR program for these fragment reactions was identical to the amplicon PCR program except that it utilized a total of seven rather than 25 thermal cycles.

The products from the fragment PCR reactions were diluted 1:4 by the addition of 90 μl of water. These dilutions were then used to set up the joining PCR reactions. These reactions contained 15 μl of 2×KOD Hot Start Master Mix, 4 μl of the 1:4 dilution of the forward-fragment reaction, 4 μl of the 1:4 dilution of the reverse-fragment reaction, 2 μl of 4.5 μM 5'-BsmBI-Aichi68-NP, 2 μl of 4.5 μM 3'-BsmBI-Aichi68-NP, and 3 μl of water. The PCR program for these joining reactions was identical to the amplicon PCR program except that it utilized a total of 20 rather than 25 thermal cycles. The products from these joining PCR programs were then purified over agarose gels.

The purified products of the first joining PCR reaction was used as templates for a second round of fragment PCR reactions followed by a second joining PCR reaction. These second-round products were purified over agarose gels, and then used as templates for a third round of fragment PCR reactions and joining PCR reaction. The third-round products were purified over agarose gels, digested with the restriction enzyme BsmBI (New England Biolabs, Ipswich, Mass.), and ligated into a dephosphorylated (Antarctic Phosphatase, New England Biolabs) BsmBI digested pHW2000 plasmid (Hoffmann et al., *Proc. Nat'l. Acad. Sci. USA* 97:6108, 2000) using T4 DNA ligase (Invitrogen, Grand Island, N.Y.).

The nucleic acid molecule ligation products were purified using ZymoClean columns, electroporated into ElectroMAX DH10B T1 phage-resistant competent *E. coli* (Invitrogen), spread on LB plates supplemented with 100 μg/ml ampicillin, and incubated at 37° C. overnight. These transformations yielded between 400,000 and 800,000 unique transformants per plate, as judged by plating a 1:4,000 dilution of the transformations on a second set of plates. Transformation of a parallel no-insert control ligation yielded approximately 50-fold fewer colonies, indicating that self-ligation of the digested pHW2000 plasmid only accounts for a small fraction of the transformants. For each library replicate, three transformations were performed, grown on LB plates overnight, and then the colonies were scraped into liquid LB supplemented with ampicillin and DNA isolated four hours later to yield the mutant plasmid libraries. These libraries contain well in excess of $10^6$ unique transformants, most of which will correspond to unique codon mutants of the influenza NP gene.

To assess the quality of the codon-mutant libraries, the full NP gene for 30 individual clones was sequenced. The Sanger-sequenced clones contained an average of 2.7 codon mutations per gene, and a negligible number of insertions/deletions (0.1 per gene). As shown in FIG. 1, the number of mutations per clone was approximately Poisson distributed and the mutations occurred uniformly along the primary sequence of the NP gene. If all codon mutations are made with equal probability, it is expected that 9 out of 63 mutations to be single nucleotide changes, 27 out of 63 mutations to be two-nucleotide changes, and 27 out of 63 mutations to be three-nucleotide changes. This is approximately what was observed in our Sanger-sequenced clones (FIG. 1), although there may be a slight elevation in single-nucleotide codon changes, which may be due to additional mutations that arise as a consequence of the PCR process.

The nucleotide composition of the mutated codons is roughly uniform, and there is no tendency for clustering of multiple mutations in the primary sequence (FIG. 1).

Figure 1A:
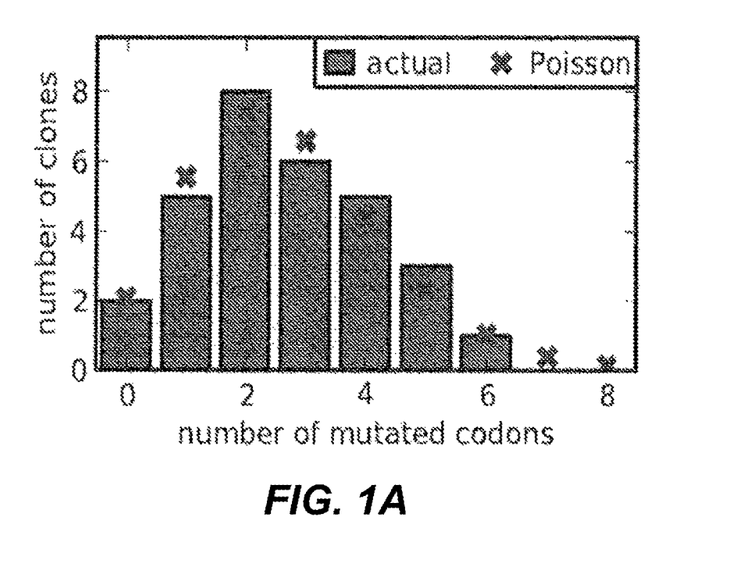
FIGS. 1A-1E show the properties of a codon-mutant library of the influenza nucleoprotein (N ing errors and codon mutations in the mutDNA samples, explaining why they are somewhat higher than the values estimated by Sanger sequencing.
Figure 1B:
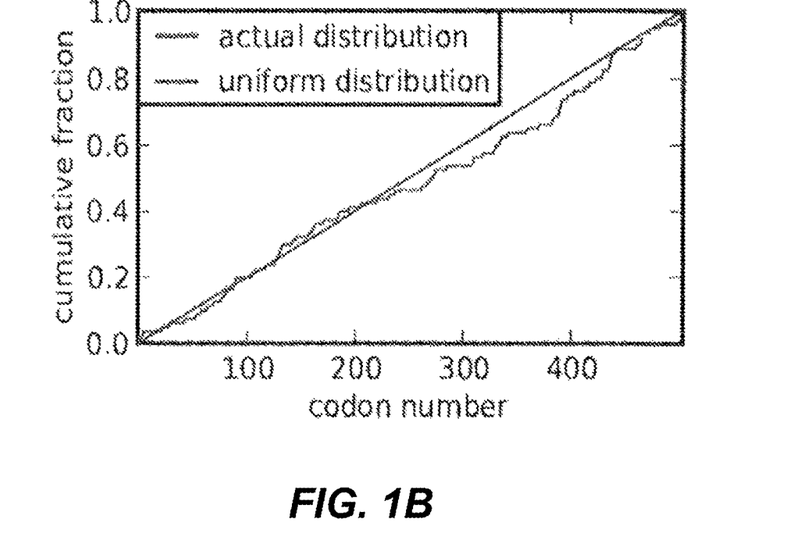
Figure 1C:
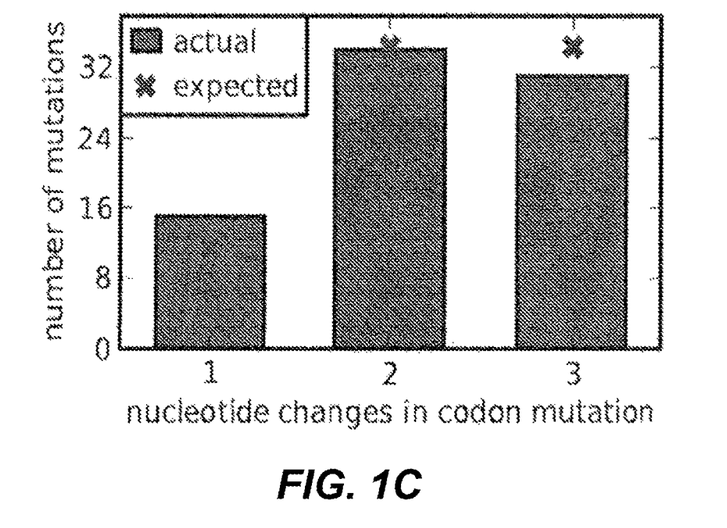
Figure 1D:
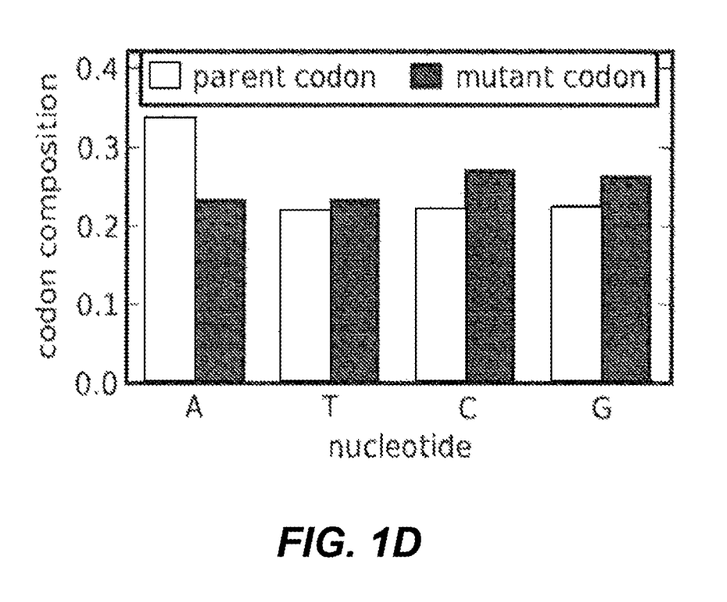
Figure 1E:
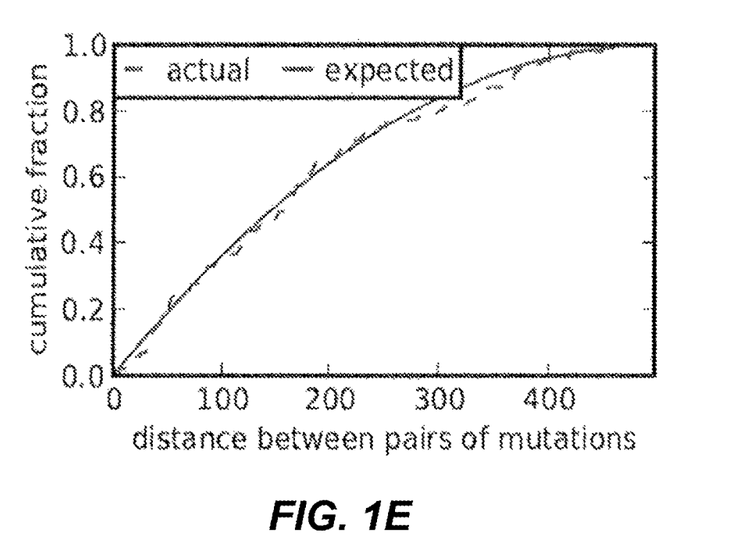
Figure 2:
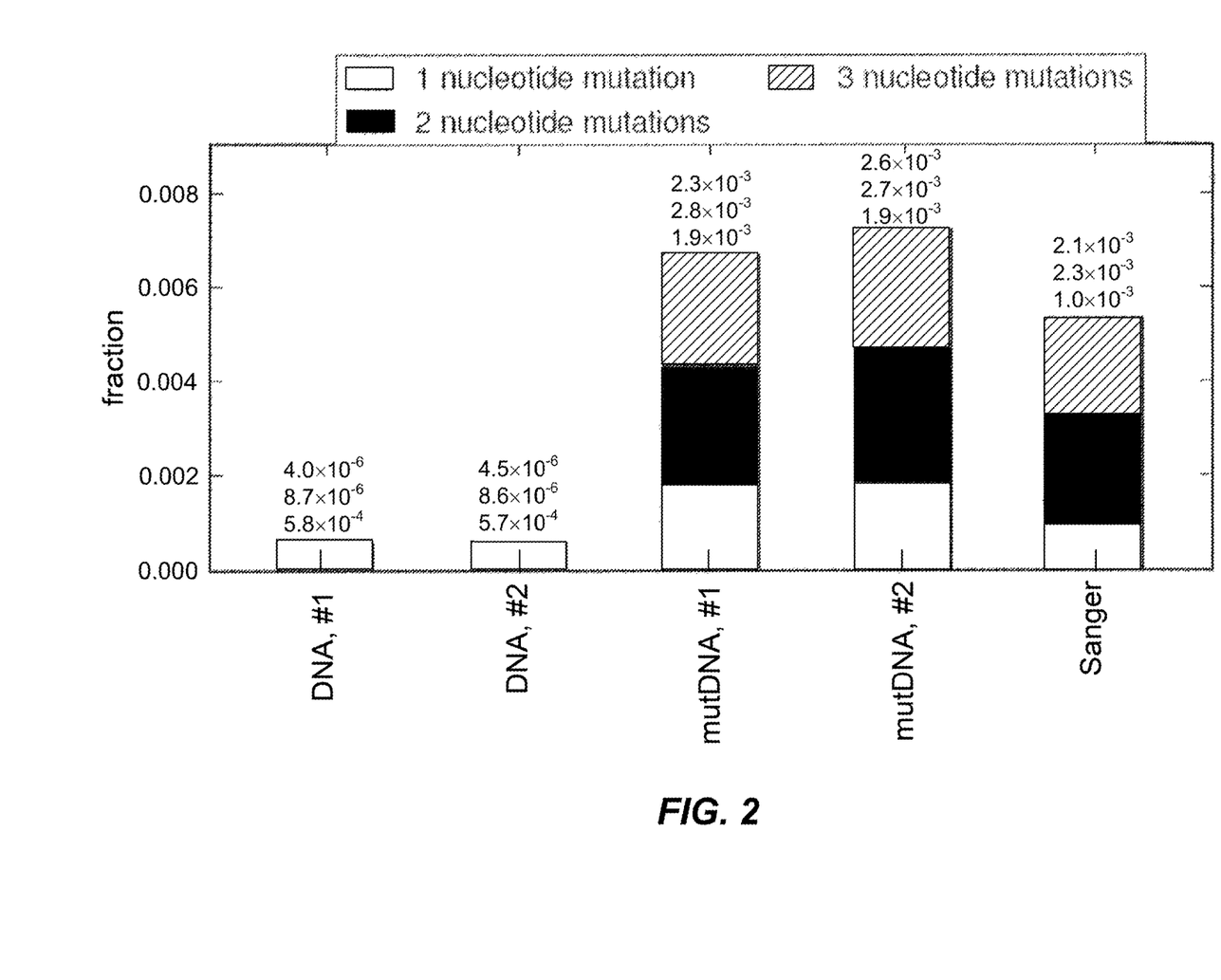
Figure 3A:
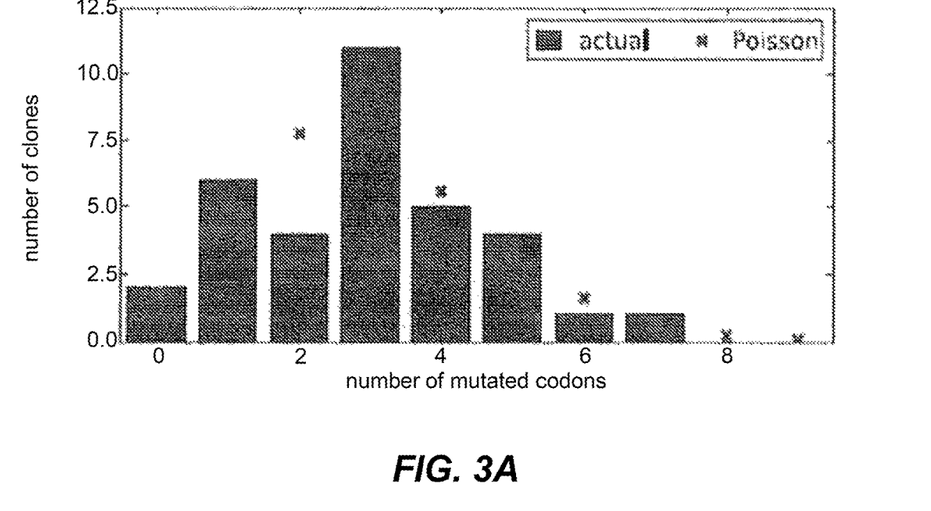
FIGS. 3A-3E show the properties of a codon-mutant library of the influenza hemagglutinin (HA) gene as assessed by Sanger sequencing of 34 clones. The plots of (A) to (E) parallel the analysis and data shown FIG. 1.
Figure 3B:
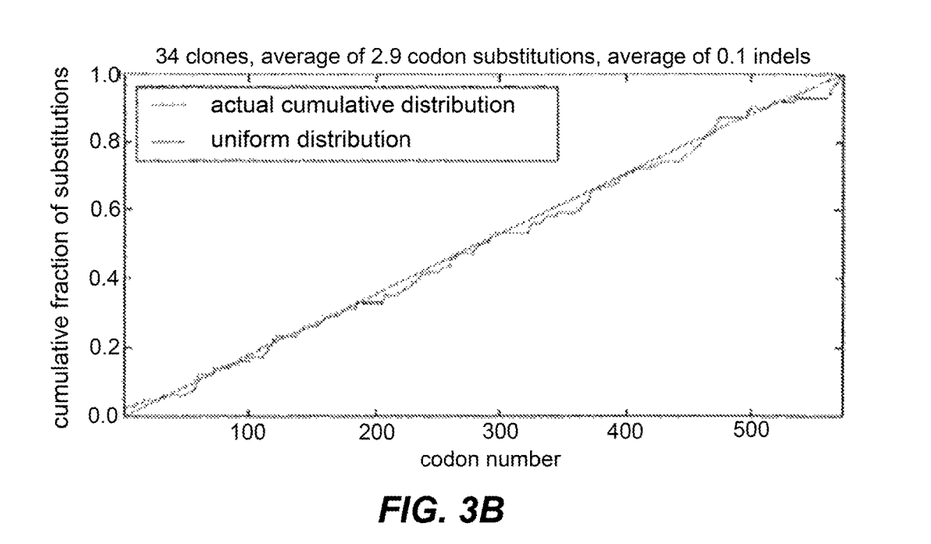
Figure 3C:
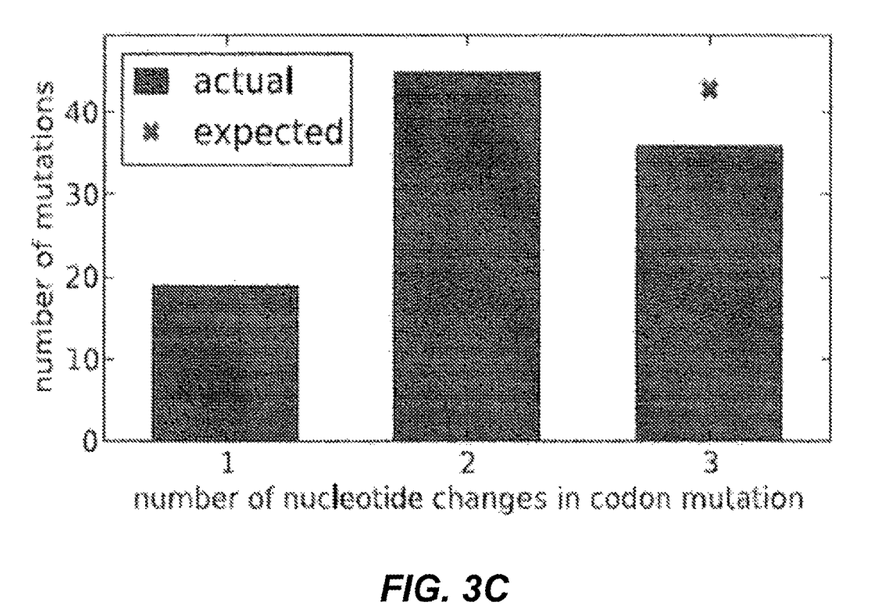
Figure 3D:
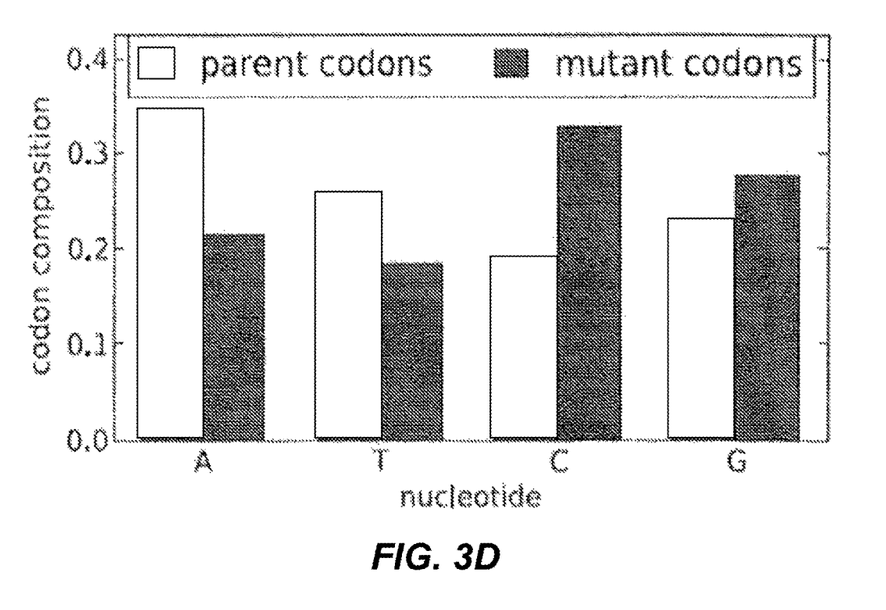
Figure 3E:
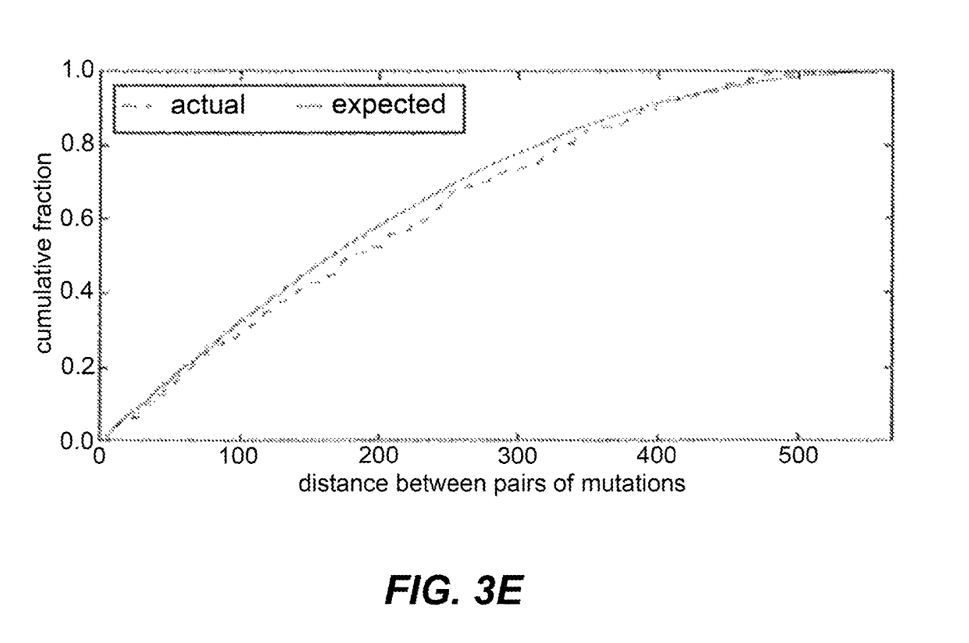

To further characterize the library, Illumina (San Diego, Calif.) deep-sequencing was used to quantify the rate of single, double, and triple nucleotide mutations in duplicate preparations of this library. The results are shown in FIG. 2, and corroborate the codon-mutation rates estimated by the Sanger sequencing of the 30 selected clones.

Example 2

Construction of Influenza HA Codon-Mutant Libraries

To demonstrate the generality of our approach, we created a second codon mutant library of the 1,698-nucleotide influenza hemagglutinin (HA) gene using the same technique as described in Example 1. The results of Sanger sequencing 34 clones are shown in FIG. 3. As can be seen from this figure, the library had similar properties to those for the NP library, demonstrating that the approach is generally applicable.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method for making a plurality of variant nucleic acid molecules, comprising
   (a) amplifying a reference nucleic acid molecule template with a plurality of forward mutagenic oligonucleotides to produce a first plurality of forward mutagenic fragments and separately amplifying the reference nucleic acid molecule template with a plurality of reverse mutagenic oligonucleotides to produce a first plurality of reverse mutagenic fragments, wherein the reference nucleic acid molecule template comprises a plurality of codons that encode a reference polypeptide and wherein each of the plurality of forward and reverse mutagenic oligonucleotides comprise a codon randomized at one to three nucleotides and the oligonucleotides comprise from nine to 100 nucleotides, and wherein the randomized codons correspond to all codons of the reference nucleic acid molecule template except the initiation codon;

(b) purifying the first plurality of forward and reverse mutagenic fragments and mixing the purified first plurality of forward and reverse mutagenic fragments to produce a first mixed mutagenic nucleic acid molecule fragment template composition; and (c) joining the mixed nucleic acid molecule fragments of the first mixed mutagenic nucleic acid molecule fragment template composition by amplifying in a single reaction with the plurality of forward and reverse mutagenic oligonucleotides from step (a) to produce a first plurality of joined mutagenic nucleic acid molecules;

thereby introducing codon variants at random locations at a controlled mutation rate across the length of the reference nucleic acid molecule template.

2. The method according to claim 1, wherein the method further comprises purifying the first plurality of joined mutagenic nucleic acid molecules and repeating steps (a) through steps (c) of claim 1 to produce a second plurality of joined mutagenic nucleic acid molecules.

3. The method according to claim 2, wherein the method further comprises purifying the second plurality of joined mutagenic nucleic acid molecules and repeating steps (a) through steps (c) of claim 1 to produce a third plurality of joined mutagenic nucleic acid molecules.

4. The method according to claim 3, wherein the method further comprises repeating steps (a) through steps (c) of claim 1 at least 3, 4, 5, 6, 7, 8, 9, 10 or more times by purifying the plurality of joined mutagenic nucleic acid molecules generated in the previous round of the method and performing steps (a) through steps (c).

5. The method according to claim 1, further comprising the step of amplifying the reference nucleic acid molecule template before step (a) of claim 1 with an oligonucleotide complimentary to the 5'-end of the reference nucleic acid molecule template and with an oligonucleotide complimentary to the 3'-end of the reference nucleic acid molecule template, wherein the 5'-end and 3'-end oligonucleotides comprise a sequence recognized by a restriction endonuclease to produce an end-modified reference nucleic acid molecule template; and purifying the end-modified reference nucleic acid molecule template.

6. The method according to claim 1, wherein the randomized codon of the forward and reverse mutagenic oligonucleotides is NNN, YTN, NTN, NNW, NNS, NNM, NNK, NNR, NNB, NND, NNV, NNH, BBB, DDD, VVV, HHH, NNA, NNT, NNC, NNG, NAN, NCN, NGN, ANN, TNN, CNN, GNN or any combination thereof.

7. The method according to claim 1, wherein the randomized codon of the forward and reverse mutagenic oligonucleotides is located in the middle of the oligonucleotide, near the 5'-end of the oligonucleotide, near the 3'-end of the oligonucleotide, or any combination thereof.

8. The method according to claim 1, wherein the forward mutagenic oligonucleotide, reverse mutagenic oligonucleotide, or both individually comprise from about 20 to about 50 nucleotides.

9. The method according to claim 1, wherein the codon variants at random locations across the length of the reference nucleic acid molecule template comprise a number of mutations and the number of mutations per reference nucleic acid molecule template follows an approximate Poisson distribution.

10. The method according to claim 1, wherein the codon variants at random locations across the length of the reference nucleic acid molecule template comprise mutations that occur uniformly along the length of the reference nucleic acid molecule template.

11. The method according to claim 1, wherein the codon variants at random locations across the length of the reference nucleic acid molecule template comprise a uniform base composition.

12. The method according to claim 1, wherein the reference nucleic acid molecule templates comprises multiple mutations that are not clustered.

13. The method according claim 1, wherein the number of codon variants introduced comprises from about one to about ten different mutants.

14. The method according to claim 1, wherein the method results in no more than 0.5 insertions, deletions, or a combination thereof per reference nucleic acid molecule.

15. The method according to claim 1, wherein the reference nucleic acid molecule is an animal, viral, bacterial, fungal, plant, protist, or archaebacterial gene.

16. The method according to claim 15, wherein the viral gene is an influenza gene.

17. The method according to claim 16, wherein the influenza gene is a nucleoprotein or hemagglutinin gene.

18. The method according to claim 1, wherein the forward mutagenic oligonucleotide, reverse mutagenic oligonucleotide, or both individually comprise non-coding sequence from the reference nucleic acid molecule template.

* * * * *